(12) United States Patent
Nelson et al.

(10) Patent No.: US 8,113,037 B2
(45) Date of Patent: Feb. 14, 2012

(54) METHOD FOR TESTING HIGH TEMPERATURE MECHANICAL DURABILITY OF ARTICLES

(75) Inventors: Warren Arthur Nelson, Schenectady, NY (US); Yuk-Chiu Lau, Ballston Lake, NY (US); Joshua L. Margolies, Niskayuna, NY (US)

(73) Assignee: General Electric Company, Schenectady, NY (US)

( * ) Notice: Subject to any disclaimer, the term of this patent is extended or adjusted under 35 U.S.C. 154(b) by 445 days.

(21) Appl. No.: 12/413,757

(22) Filed: Mar. 30, 2009

(65) Prior Publication Data
US 2010/0242580 A1 Sep. 30, 2010

(51) Int. Cl.
*G01N 17/00* (2006.01)
(52) U.S. Cl. .......................................................... 73/86
(58) Field of Classification Search ......... 73/86, 112.01, 73/150 R, 865.5, 866
See application file for complete search history.

(56) References Cited

U.S. PATENT DOCUMENTS

| 5,732,467 | A | 3/1998 | White et al. |
| 6,660,405 | B2 | 12/2003 | Lau et al. |
| 6,887,528 | B2 | 5/2005 | Lau et al. |
| 7,166,373 | B2 | 1/2007 | Spitsberg et al. |
| 7,476,453 | B2 | 1/2009 | Rohrer Boutwell et al. |
| 7,537,806 | B2 | 5/2009 | Boutwell et al. |

OTHER PUBLICATIONS

Davis, J.R. (2004). Handbook of Thermal Spray Technology. (pp. 8, 108, 109, 115-118, 123-125, 131, 181-182). ASM International.*
Cramer, Stephen D.; Covino, Bernard S., Jr. (2003). ASM Handbook, vol. 13A—Corrosion: Fundamentals, Testing, and Protection. (pp. 641-642). ASM International.*

* cited by examiner

*Primary Examiner* — Hezron E Williams
*Assistant Examiner* — Jamar Ray
(74) *Attorney, Agent, or Firm* — Nixon & Vanderhye, P.C.

(57) ABSTRACT

A process for erosion testing of a specimen article includes securing a test specimen in a test rig; measuring physical characteristics of the test specimen article; using a thermal spray coating apparatus, flowing incident particles at the test specimen; and re-measuring the physical characteristics of the test specimen.

18 Claims, 2 Drawing Sheets

METHOD FOR TESTING HIGH TEMPERATURE MECHANICAL DURABILITY OF ARTICLES

This invention relates to a method of conducting erosion tests on materials or coatings, for example, turbine buckets with thermal barrier coatings applied to some or all of the surfaces of the bucket.

BACKGROUND OF THE INVENTION

Hot impact/erosion test facilities typically include custom test rigs that are labor intensive to set up and expensive to run and maintain. They typically include a combustion system and a particle delivery system, and, in fact, there are relatively few such systems available—most are located at universities or other research institutions. On the other hand, there is a large installed base of systems for applying coatings to various industrial components, including high temperature components such as turbine buckets or blades. These systems typically employ any one of several well-known thermal spraying techniques to apply various coatings to such components. This invention seeks to take advantage of the various known thermal spray coating systems by using them to conduct hot impact/erosion testing to determine the durability of the component coatings (or of non-coated component materials).

BRIEF SUMMARY OF THE INVENTION

In one exemplary but nonlimiting aspect, the invention relates to a process for erosion testing of a test specimen comprising securing the specimen article in a test rig; measuring physical characteristics of the specimen article; using a thermal spray coating apparatus, projecting incident particles of specified size, composition, temperature and velocity at the specimen article; and re-measuring the physical characteristics of the specimen article.

In another exemplary but nonlimiting aspect, the invention relates to a process for erosion testing of a coating on a turbine component comprising securing the turbine component in a test rig; measuring physical characteristics of the turbine component; heating the turbine component to its normal service temperature; using a thermal spray coating apparatus, flowing hot incident particles at the turbine component; and re-measuring the physical characteristics of the turbine component.

The invention will now be described in detail in connection with the drawings identified below.

DETAILED DESCRIPTION OF THE DRAWINGS

Figure 1:
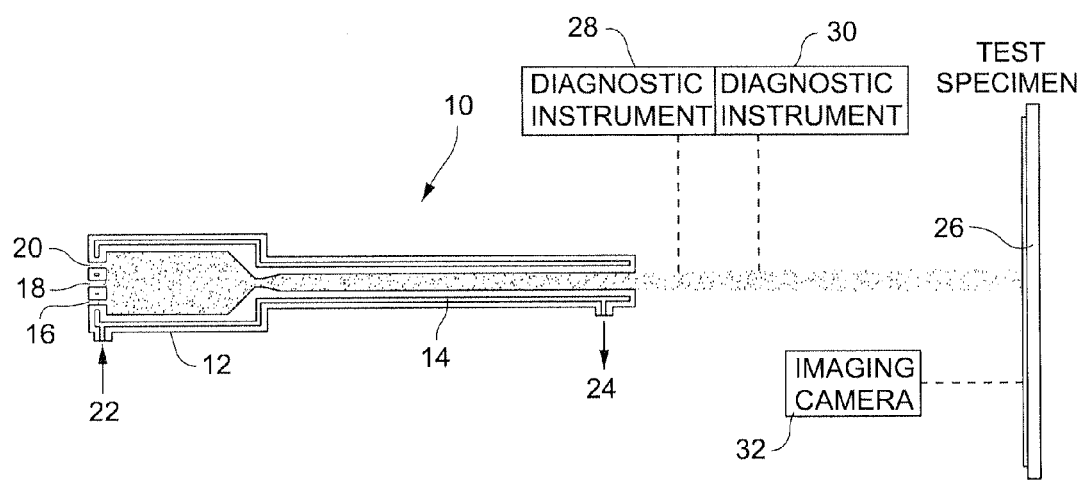
FIG. 1 is a side elevation in partly schematic form, of a thermal spray apparatus used in accordance with an exemplary embodiment of the invention.

With reference to FIG. 1, an apparatus for high temperature durability testing may include a High Velocity Oxygen Fuel (HVOF) thermal spray gun 10. The gun 10 is formed to include a combustion chamber 12 and a long nozzle 14. Inlets 16, 18 and 20 supply fuel, powder and oxygen, respectively to the combustion chamber. Cooling water circulates about the gun via inlet 22 and outlet 24. The test (or target) specimen or component (also referred to herein as a "specimen article") is shown at 26. In the process described herein, the test specimen is a turbine bucket but it will be appreciated that the test specimen 26 be any component or test specimen that can be accommodated by the HVOF (or equivalent thermal spray coating) system.

The HVOF thermal spray gun 10 may be of conventional construction and need not be described in further detail here. It is sufficient to note that fuel (such as kerosene, acetylene, propylene or hydrogen) and oxygen are supplied to the combustion chamber 12 where the combustion process produces a hot, high-pressure flame that travels at increasing velocity through the nozzle 14. Typically, a powder is fed axially into the combustion chamber 12 via inlet 18 under high pressure and exits the nozzle, coating the target component. During this process, it will be appreciated that the gun 10 is typically moved automatically back and forth across the target to provide a uniform coating on the target.

In an exemplary but nonlimiting implementation of this invention, however, the powder feeder is modified to deliver, for example, 250 micron alumina grit or other controlled size incident particles (greater than about 120 micron) such as yttria stabilized zirconia powder (−35+48 mesh) in a process described in further detail below. Such a coarse particle size is not typical of commercial thermal spray coating processes in which the typical size is 50 microns. The erodent or incident particle size and composition can be tailored to reproduce or simulate a desired service condition (e.g. runway dust, airborne flyash, IGCC combustion by-products, etc.).

More specifically, the modified HVOF thermal spray coating gun is used to conduct hot impact and erosion tests on coated or non-coated specimens. The HVOF gun heats and accelerates the incident particles toward the test specimen 26, which has been preheated to its normal service temperature. For the purposes of erosion or impact testing the particle temperature is generally controlled to below its melting temperature e.g., 0.9 of the melting temperature, to prevent deposition onto the coating. In another embodiment of the invention, the incident particle temperature is controlled to produce a semi-molten state to evaluate potential chemical interactions between the incident particle material and the test surface.

In addition, particle diagnostic instruments 28, 30 (such as, for example, the DVP 2000 or Accuraspray systems available from Tecnar Automation Ltee of St. Bruno, QC, Canada), are used to measure the temperature and velocity of the particles in flight. The operating parameters of the HVOF system can be adjusted to control the impacting particle temperature and velocity based on measurements from the diagnostic instruments for various compositions and particle sizes. The test specimen temperature, stand-off distance, and angle of particle impingement are also easily controlled. In this regard, a thermal imaging camera 32 may be used to monitor surface temperature of the test specimen. Other methods of monitoring surface temperature of the test specimen are thermocouples or thermal paints.

Figure 2:
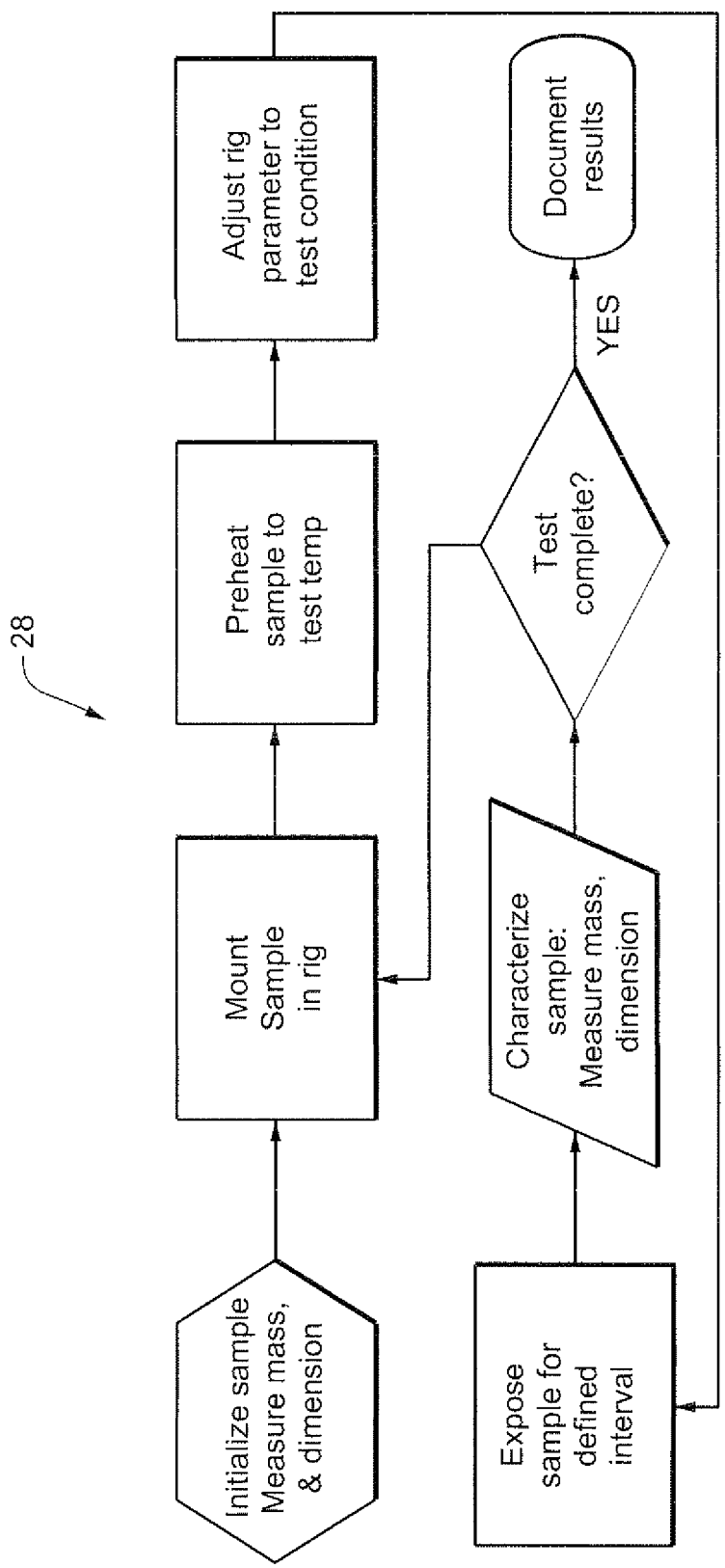
FIG. 2 is a process flow diagram of an exemplary embodiment of the invention.

FIG. 2 is a process flowchart indicating the various steps of the exemplary process. In the event the test relates to the durability or erosion resistance of a coating on, for example, a turbine component such as a blade or bucket, the test specimen blade coating is initially characterized before the test with a Mass Balance and Laser Micrometer for thickness, mass and surface roughness. The test specimen is then mounted in a test rig (in the same manner as an article to be coated) and secured. The test specimen is then heated to its rated (normal) service temperature to insure that the test is relevant to the operating conditions of the specimen, in this case, the hot gas flow path in which the turbine blade is located. Further in this regard, the test rig may be adjusted so that the incident particles strike the blade at substantially the same angle and at substantially the same velocity as particles might strike the blade in normal operating conditions. In this regard the impact angle and velocity vary from compressor inlet to combustion to turbine stages.

After exposure to the particles projected by the thermal spray gun for some preset time (or number of passes, e.g. three, six, nine etc.), the test specimen coating is again inspected and any changes in thickness, mass and surface roughness are noted and the resistance to damage from the hot incident particle stream is ranked and documented. Iterations are performed until the coating material reaches some threshold exposure time/performance plateau.

While the above-exemplary process uses an HVOF spray gun, the invention is not is any way limited to a single type of thermal spray apparatus. Other thermal spray apparatus suitable for use in the disclosed process include plasma spray, detonation spray, flame spray, HVAF (High Velocity Air Fuel), vacuum plasma spray, cold spray, etc.

SPECIFIC EXAMPLE

Samples were prepared with plasma sprayed thermal barrier coatings (TBCs). A Praxair/TAFA JP-5000 liquid fuel HVOF torch was set up with a powder feeder modified to deliver ~0.25 mm dia. alumina grit rather than the more conventional fine thermal spray powder (~0.05 mm max dia). This erodent or incident particle size is beyond the capability of standard powder feed equipment and modification was required. The Tecnar DPV-2000 diagnostic instrument was set up to measure the in-flight temperature and velocity of the alumina grit in the JP-5000 spray plume. A FLIR thermal imaging camera was set up to monitor the surface temperature of the TBC coated samples. The HVOF torch parameters were then adjusted to produce a coated sample temperature of approximately 2000° F., and a second parameter developed to produce an in-flight particle velocity of 600 m/sec and a particle temperature below the creep range of the incident particles (in this example, below 1800° F.). The coating samples were measured for mass and thickness before initiation of testing. Surface roughness was not measured in the initial feasibility demonstration. One sample was subjected to 3 passes of the alumina grit, another to 6 passes, and a third to 9 passes. Each was measured for thickness and mass after testing. It was clear that longer exposure led to greater mass and thickness loss. It will be appreciated as noted above that the incident particle size, temperature, velocity and angle of impact may vary depending on the specific operating condition of interest.

The hot impact/erosion testing described herein, using off-the-shelf thermal spray system, provides an affordable, reliable and flexible arrangement that eliminates the need for custom, dedicated test rigs. While the above example used the HVOF torch to heat the test specimen other methods, such as quartz lamps, induction heating, or a second torch could be used to heat the test specimen.

It will also be appreciated that the test method described herein may be used in quality control applications where component or coating quality may be verified prior to release of the components for use in customer turbines.

While the invention has been described in connection with what is presently considered to be the most practical and preferred embodiment, it is to be understood that the invention is not to be limited to the disclosed embodiment, but on the contrary, is intended to cover various modifications and equivalent arrangements included within the spirit and scope of the appended claims.

What is claimed is:

1. A process for erosion testing of a specimen article comprising:
    (a) securing the specimen article in a test rig;
    (b) measuring physical characteristics of the specimen article;
    (c) using a thermal spray coating apparatus, projecting incident erodent particles of specified size, composition, temperature and velocity at the specimen article; and
    (d) re-measuring the physical characteristics of the specimen article to thereby determine erosive effect of step (c) on said specimen article; and prior to step (c), heating the specimen article to a specified test temperature substantially equal to a normal service temperature of said specimen article.

2. The process of claim 1 wherein the thermal spray apparatus is chosen from a group comprising HVOF, detonation, plasma, flame HVAF, vacuum plasma spray, and cold spray.

3. The process of claim 1 including, during step (c), monitoring and controlling the temperature and velocity of the incident erodent particles.

4. The process of claim 1 including, during step (c), monitoring and controlling the temperature and velocity of the incident erodent particles and monitoring and controlling temperature of the specimen article.

5. The process of claim 4 wherein the specimen article temperature is greater than 2000° F., and the incident erodent particle temperature is below the creep range of incident erodent particle material.

6. The process of claim 1 wherein said specimen article is a turbine blade.

7. The process of claim 1 wherein step (c) is carried out in plural repetitive passes.

8. The process of claim 1 wherein said incident erodent particles have a diameter greater than 120 microns.

9. A process for erosion-testing of a coating on a turbine component comprising:
    (a) securing the turbine component in a test rig;
    (b) measuring physical characteristics of the turbine component including at least a thickness of said coating;
    (c) heating the turbine component to its normal service temperature;
    (d) using a thermal spray coating apparatus, flowing hot, incident erodent particles at the turbine component; and
    (e) re-measuring the physical characteristics of the turbine component including the thickness of said coating to thereby determine erosive effect of step (d) on said coating.

10. The process of claim 9 wherein the thermal spray apparatus is chosen from a group comprising HVOF, detonation, plasma, flame HVAF, vacuum plasma spray and cold spray.

11. The process of claim 9 including, during step (d), monitoring and controlling the temperature and velocity of the incident erodent particles.

12. The process of claim 9 including, during step (d), monitoring and controlling the temperature of the turbine component.

13. The process of claim 9 including, during step (d), monitoring and controlling the temperature and velocity of the incident erodent particles and temperature of the turbine component.

14. The process of claim 9 wherein said incident erodent particles have a diameter of greater than 120 microns.

15. The process of claim 9 wherein the turbine component temperature is greater than 2000° F., and the incident erodent particle temperature is below the creep range the incident erodent particle material.

16. The process of claim 15 wherein said turbine component comprises a turbine blade.

17. The process of claim 9 wherein said turbine component comprises a turbine blade.

18. The process of claim 9 wherein said physical characteristics of said turbine component include mass and surface roughness.

* * * * *